(12) United States Patent
Shuman et al.

(10) Patent No.: US 6,544,220 B2
(45) Date of Patent: Apr. 8, 2003

(54) FLUID JET PMR

(75) Inventors: Brandon J. Shuman, Kirkland, WA (US); Tim Johnson, Seatac, WA (US); Joseph Pearce, Seattle, WA (US); Zihong Guo, Bellevue, WA (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/780,698

(22) Filed: Feb. 14, 2001

(65) Prior Publication Data

US 2002/0111644 A1 Aug. 15, 2002

(51) Int. Cl.[7] .............................................. A61M 29/00
(52) U.S. Cl. ................. 604/99.04; 604/249; 251/129.06
(58) Field of Search ........................... 128/898; 251/12, 251/129.06, 903; 604/246, 247, 248, 249, 256, 96.01, 232, 509, 93.01, 95.03, 95.05, 99.04, 101.01, 101.05, 103.06, 104, 912, 511

(56) References Cited

U.S. PATENT DOCUMENTS

| | | | |
|---|---|---|---|
| 4,019,515 A | * | 4/1977 | Kornblum et al. .......... 128/246 |
| 5,030,210 A | * | 7/1991 | Alchas ........................ 604/247 |
| 5,059,176 A | * | 10/1991 | Winters ........................ 604/96 |
| 5,451,224 A | | 9/1995 | Goble et al. ................... 606/48 |
| 5,593,406 A | | 1/1997 | Eggers et al. ................. 606/46 |
| 5,697,882 A | | 12/1997 | Eggers et al. ............... 604/114 |
| 5,725,523 A | * | 3/1998 | Mueller ........................ 604/15 |
| 5,766,164 A | | 6/1998 | Mueller et al. ................ 606/15 |
| 5,769,843 A | | 6/1998 | Abela et al. ................... 606/10 |
| 5,782,823 A | | 7/1998 | Mueller ......................... 606/7 |
| 5,785,702 A | | 7/1998 | Murphy-Chutorian et al. . 606/7 |
| 5,800,450 A | | 9/1998 | Lary et al. ................... 606/180 |
| 5,807,384 A | | 9/1998 | Mueller ......................... 606/7 |
| 5,807,388 A | | 9/1998 | Jeevanandam et al. ....... 606/15 |

(List continued on next page.)

FOREIGN PATENT DOCUMENTS

| | | |
|---|---|---|
| EP | 0 868 923 A2 | 10/1998 |
| WO | WO 98/19614 | 5/1998 |
| WO | WO 98/25533 | 6/1998 |
| WO | WO 98/27877 | 7/1998 |
| WO | WO 98/30144 | 7/1998 |
| WO | WO 98/31281 | 7/1998 |
| WO | WO 98/33557 | 8/1998 |
| WO | WO 98/38916 | 9/1998 |
| WO | WO 98/38925 | 9/1998 |
| WO | WO 98/39038 | 9/1998 |
| WO | WO 98/49963 | 11/1998 |
| WO | WO 98/49964 | 11/1998 |
| WO | WO 99/04708 | 2/1999 |
| WO | WO 99/04709 | 2/1999 |
| WO | WO 99/07296 | 2/1999 |
| WO | WO 99/08612 | 2/1999 |

Primary Examiner—Gene Mancene
Assistant Examiner—Patrick Buechner
(74) Attorney, Agent, or Firm—Christensen O'Connor Johnson Kindness PLLC (57) ABSTRACT

A system for performing fluid jet myocardial revascularization includes a catheter having a proximal region, a distal region, a lumen extending therethrough and a valve disposed in the lumen for allowing the passage of fluids in the lumen to create holes in the myocardium. A valve control means extends through the proximal region of the catheter to open and close the valve. In one embodiment, the valve also includes a biasing mechanism for biasing the valve in a closed position. The valve may be controlled using an electrically actuated device that is heated with an electrical current to open and close the valve. In one embodiment of the invention, the catheter has a wall that can be expanded within a guide catheter to anchor the catheter during revascularization.

9 Claims, 5 Drawing Sheets

U.S. PATENT DOCUMENTS

| | | | |
|---|---|---|---|
| 5,810,836 A | 9/1998 | Hussein et al. | 606/108 |
| 5,827,203 A | 10/1998 | Nita | 601/2 |
| 5,832,929 A | 11/1998 | Rudko et al. | 128/898 |
| 5,840,059 A | 11/1998 | March et al. | 604/53 |
| 5,840,075 A | 11/1998 | Mueller et al. | 606/7 |
| 5,855,577 A | 1/1999 | Murphy-Chutorian et al. | 606/7 |
| 5,860,951 A | 1/1999 | Eggers et al. | 604/49 |
| 5,871,469 A | 2/1999 | Eggers et al. | 604/114 |
| 5,871,495 A | 2/1999 | Mueller | 606/185 |
| 5,873,366 A | 2/1999 | Chim et al. | 128/898 |
| 5,873,855 A | 2/1999 | Eggers et al. | 604/114 |
| 5,878,751 A | 3/1999 | Hussein et al. | 128/898 |
| 5,885,272 A | 3/1999 | Aita et al. | 606/7 |
| 5,885,276 A | 3/1999 | Ammar et al. | 606/21 |
| 5,891,133 A | 4/1999 | Murphy-Chutorian | 606/7 |
| 5,893,848 A | 4/1999 | Negus et al. | 606/41 |
| 5,906,615 A | 5/1999 | Thompson | 606/45 |
| 5,968,059 A | 10/1999 | Ellis et al. | 606/167 |
| 6,010,476 A * | 1/2000 | Saadat | 604/22 |
| 6,030,377 A * | 2/2000 | Linhares et al. | 606/7 |
| 6,045,531 A * | 3/2000 | Davis | 604/101 |
| 6,056,743 A | 5/2000 | Ellis et al. | 606/15 |
| 6,066,134 A | 5/2000 | Eggers et al. | 606/32 |
| 6,093,185 A | 7/2000 | Ellis et al. | 606/28 |
| 6,120,476 A | 9/2000 | Fung et al. | 604/95 |
| 6,162,214 A | 12/2000 | Mueller et al. | 606/15 |
| 6,168,624 B1 | 1/2001 | Sudai | 623/3.21 |
| 6,198,974 B1 | 3/2001 | Webster, Jr. | 607/122 |
| 6,217,575 B1 | 4/2001 | DeVore et al. | 606/41 |
| 6,224,590 B1 * | 5/2001 | Daikuzono | 606/15 |
| 6,224,592 B1 | 5/2001 | Eggers et al. | 606/32 |
| 6,319,230 B1 * | 11/2001 | Palasis et al. | 604/164.01 |
| 6,344,027 B1 * | 2/2002 | Goll | 604/68 |

* cited by examiner

FLUID JET PMR

FIELD OF THE INVENTION

The present invention is related generally to medical devices. More specifically, the present invention includes devices for performing myovascular revascularization including percutaneous myocardial revascularization (PMR).

BACKGROUND OF THE INVENTION

A number of techniques are available for treating cardiovascular disease, such as cardiovascular bypass surgery, coronary angioplasty, laser angioplasty and atherectomy. These techniques are generally applied to bypass or open lesions in coronary vessels to restore and increase blood flow to the heart muscle. In some patients, the number of lesions is so great, or the location so remote in the patient vasculature, that restoring blood flow to the heart muscle is difficult. Percutaneous myocardial revascularization (PMR) has been developed as an alternative to these techniques which are directed at bypassing or removing lesions. PMR is performed by boring holes directly into the myocardium of the heart.

PMR was inspired in part by observations that reptilian heart muscle is supplied primarily by blood perfusing directly from within heart chambers to the heart muscle. This contrasts with the human heart which is supplied by coronary vessels receiving blood from the aorta. Positive results have been demonstrated in some human patients receiving PMR treatments. These results are believed to be caused in part by blood flowing from within a heart chamber through patent holes formed by PMR to the myocardial tissue. Suitable PMR holes have been proposed to be burned by laser, cut by mechanical means, and burned by radio frequency devices. Increased blood flow to the myocardium is also believed to be caused in part by the healing response to wound formation, specifically, the formation of new blood vessels in response to the newly created wound.

What would be desirable are improved methods and devices for performing myocardial revascularization. In particular, methods allowing simultaneous hole formation in the myocardium and injection of contrast media would be advantageous. Improved methods for stabilizing myocardial revascularization catheters during use would also be desirable.

SUMMARY OF THE INVENTION

The present invention includes catheters for forming holes in the myocardium of a heart chamber wall. One catheter has a distal region, a proximal region, and an elongate tubular shaft having a lumen therethrough. A distal nozzle in fluid communication with the lumen can be disposed at the distal-most region of the catheter shaft. A fluid control valve can be disposed somewhere along the catheter shaft length for controlling fluid flow through the fluid lumen. The fluid flow through the valve can be controlled using varying devices in the various catheters.

One device includes electrical means for actuating the fluid control valve. In another device, the valve includes a biasing spring to bias the valve in a closed position, with the opening force being provided by an electrically actuated member acting to oppose the biasing spring. In one device, the electronic actuating member is a Nitinol member heated by current passing from one end to the other end through the member. In this embodiment, heating a Nitinol wire shortens the wire, which opens the valve to fluid flow. In another embodiment, a flow or control pressure lumen is provided through the catheter, with the control pressure used to open and shut the valve, thereby allowing the high pressured jet fluid to flow through the valve. In one embodiment, a needle valve is used which includes a valve stem seated within a valve seat, where the valve stem can be retracted proximally to allow flow through the valve seat. In yet another embodiment, a mechanical actuating wire is used to open the control valve. In one embodiment, an elongate control wire is operably coupled to a distal valve stem. The valve stem can have a first position for occluding flow through a valve seat, and a second position for allowing flow through the valve seat. In one device, the actuation wire is proximally retracted to allow flow, and distally extended to preclude flow. In another embodiment, a biasing spring is included within the distal region, acting to shut the valve in the absence of any applied mechanical force. In this embodiment, the actuation wire can be retracted to open the valve to fluid flow. In one embodiment, the retractable activation wire may be sufficiently strong under tension, but not compression, to open the valve.

The control valve can be located at any position along the catheter shaft length, with a preferred embodiment having a distally disposed control valve. The distally disposed control valve can allow for a relatively large inside diameter distal accumulator and orifice, while having a substantially smaller cross-section supply lumen extending the length of the catheter. This allows for a slow pressure buildup in the distal region of the catheter, followed by rapid injection of high pressure fluid into the heart wall.

One catheter includes preferentially expandable regions which expand more readily than other regions under pressure. In one example, a far distal region of a catheter device is formed of a more pliant, more easily expandable tube wall material. The more readily expanded material may inflate and expand radially under pressure. In one device, the distal-most region of the catheter is formed of a readily inflatable material. In use, the catheter formed of the more readily inflated material may be inflated to significantly increase the distal cross-sectional area of the catheter, whereupon the increased cross-sectional distal tip is forced against the heart chamber wall, for improving the seal against the heart wall. One catheter according to the present invention includes an intermediate region which is also more readily expandable than the immediate more proximal and distal regions. The expandable intermediate region can serve to anchor the fluid jet catheter within an enclosing guide catheter. The anchored catheter can more easily withstand pressures or forces which could otherwise act to shift the position of the fluid jet catheter.

Fluids which are used in the present invention can include relatively inert fluids such as saline, suitable therapeutic substances, angiogenic enhancing substances, as well as radiopaque contrast media. Adhesive agents can also be included for enhancing the retention of therapeutic substances within the heart wall. The inclusion of radiopaque contrast media allows holes to be formed and contrast media to be injected in a single step. The contrast media allows the already treated regions to be visualized under fluoroscopy by the treating physician.

DETAILED DESCRIPTION OF THE INVENTION

Figure 1:
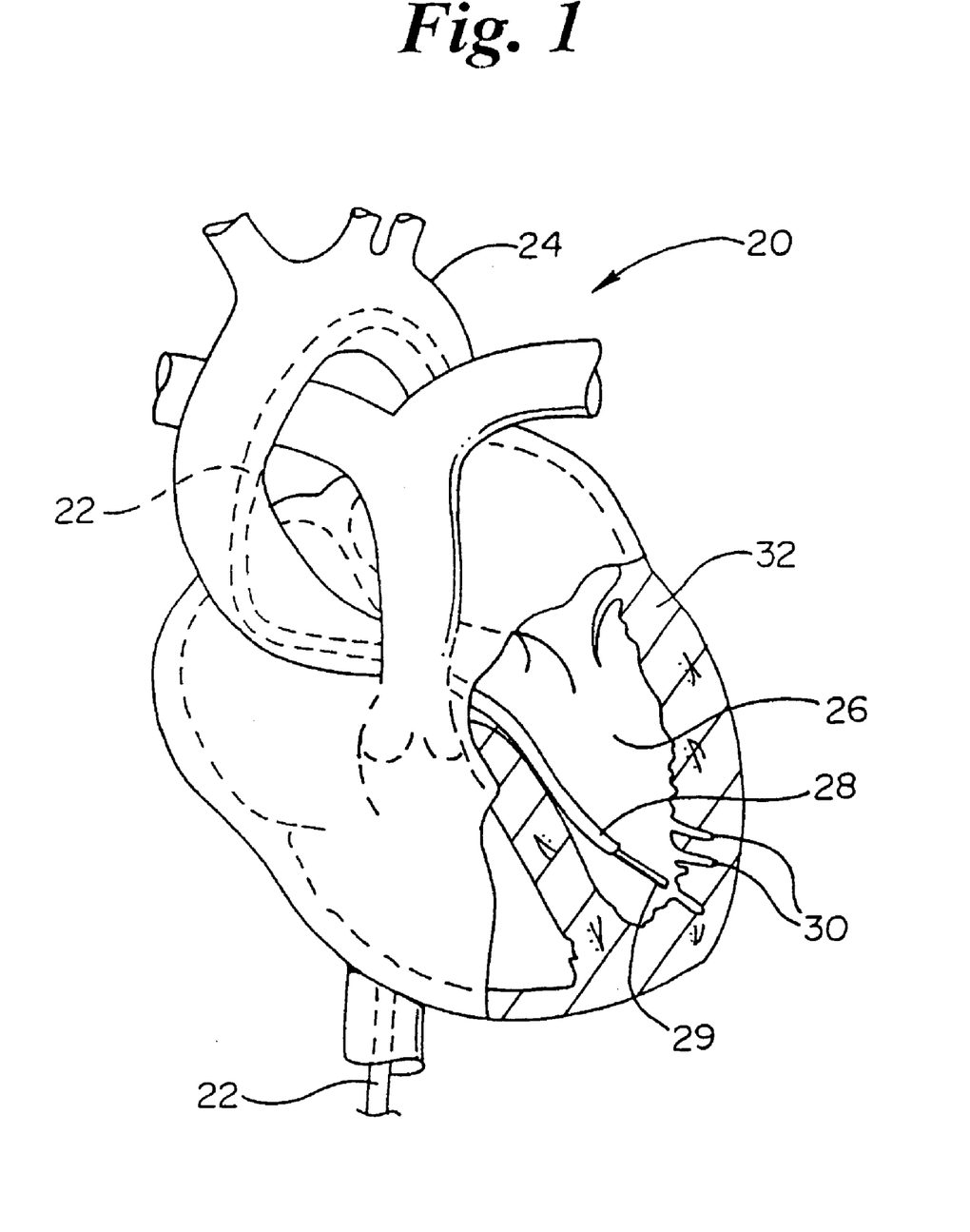
FIG. 1 is a perspective, cut-away view of a fluid jet PMR catheter disposed within a guide catheter, forming holes in the left ventricle myocardium.

FIG. 1 illustrates a heart 20 having a guide catheter 22 disposed within an aorta 24 and extending into a left ventricle 26. Guide catheter 22 is preferably a steerable catheter and can serve to contain a fluid jet PMR catheter 28 having a distal tip 29 disposed within. Fluid jet PMR distal tip 29 is shown after a plurality of channels 30 have been formed within myocardium 32. In a preferred system and method of using the present invention, fluid jet PMR catheter 28 is disposed within a guide-in-guide catheter, or tube-within-steerable-tube, catheter. For example, see U.S. Pat. No. 5,968,059 to Ellis et al., entitled TRANSMYOCARDIAL REVASCULARIZATION CATHETER AND METHOD; and U.S. Pat. No. 6,056,743 to Ellis et al., entitled PERCUTANEOUS MYOCARDIAL REVASCULARIZATION DEVICE AND METHOD, herein incorporated by reference.

Figures 2A, 2B:
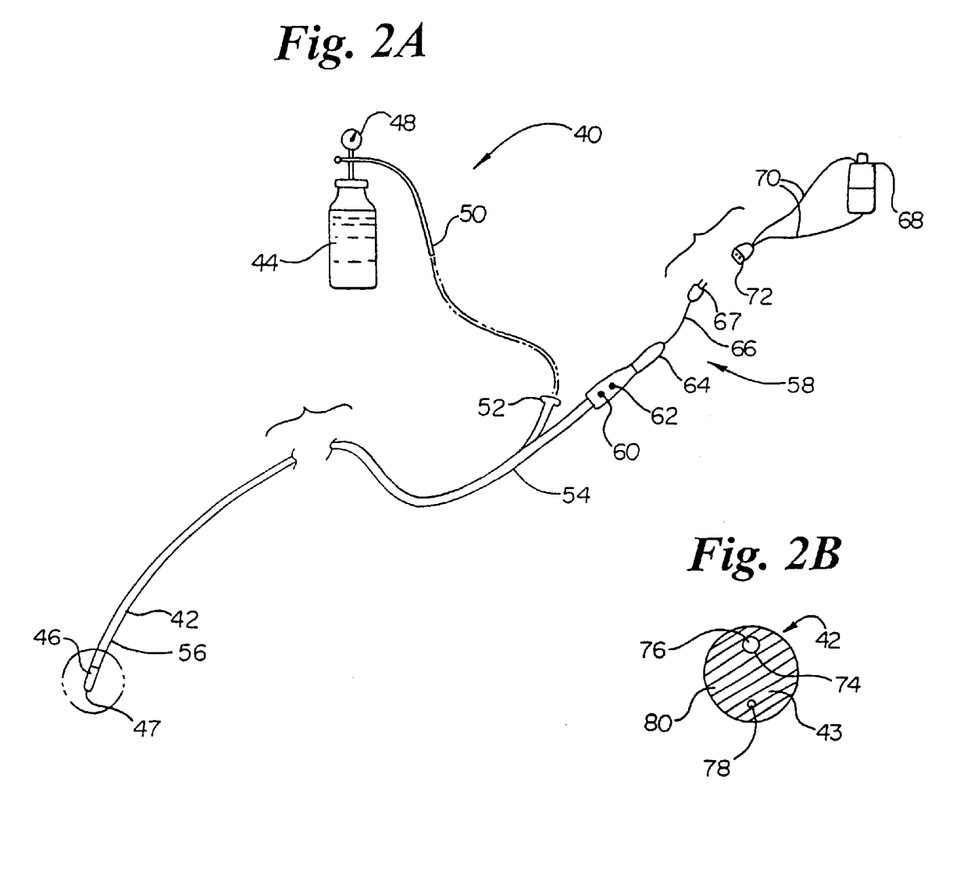
FIG. 2A is a highly diagrammatic plan view of a fluid jet PMR system.
FIG. 2B is a transverse, cross-sectional view of the fluid jet PMR catheter of FIG. 2A.

FIG. 2A illustrates a fluid jet PMR system 40 having a steerable catheter 42, which can be a guide catheter, coupled to a pressure source 44, and having a fluid jet PMR catheter 46 disposed within. Fluid jet PMR catheter 46 can terminate in a distal nozzle 47. Fluid jet system 40 includes a pressure regulator 48 for regulating pressure from pressure source or canister 44, and is coupled to a pressure supply line 50, which is in turn coupled to a pressure manifold port 52. Pressure manifold port 52 is in fluid communication with fluid jet distal nozzle 47. In the embodiment illustrated in FIG. 2A, fluid jet catheter system 40 includes a proximal region 54 and a distal region 56 on steerable catheter 42. In the embodiment shown, proximal region 54 is coupled to a proximal control assembly 58 which, in the embodiment shown, is an electrical control assembly. Proximal control assembly 58 can include an activation button 60, a safety button 62, a steering handle 64, a power supply cord 66, and a electrical plug 67. Also illustrated is a battery 68, coupled through a power cord 70, to an electrical plug 72, for joining to plug 67. Proximal control assembly 58, in the embodiment illustrated in FIG. 2A, provides electrical control signals for controlling a distal valve coupled to distal nozzle 47.

Referring now to FIG. 2B, catheter 42 is shown in a transverse cross-section. Catheter 42 can include a shaft or body 43 including a steering pull wire 78 slidably disposed therein. A pair of electrode wires 80 can also be disposed within shaft 43 to provide electrical signals to distal nozzle 47. A pressure fluid lumen 76 is also illustrated, being defined within a pressure tube 74 in the illustrated embodiment. In one device, pressure lumen 76 is defined within a metal tube, which can be formed of Nitinol. In another embodiment, lumen 76 is defined within shaft 43, not requiring a separate tube. In another embodiment, not requiring illustration, electrical wire pair 80 can be replaced or supplanted by a fluid control lumen which can be defined by a fluid control tube. In one embodiment, steerable catheter 42 includes a catheter shaft disposed within a steerable guide catheter such as a guide-in-guide catheter. In this embodiment, a steering pull wire can be provided within the guide catheter, rather than within the fluid jet PMR catheter shaft itself.

Figure 3:
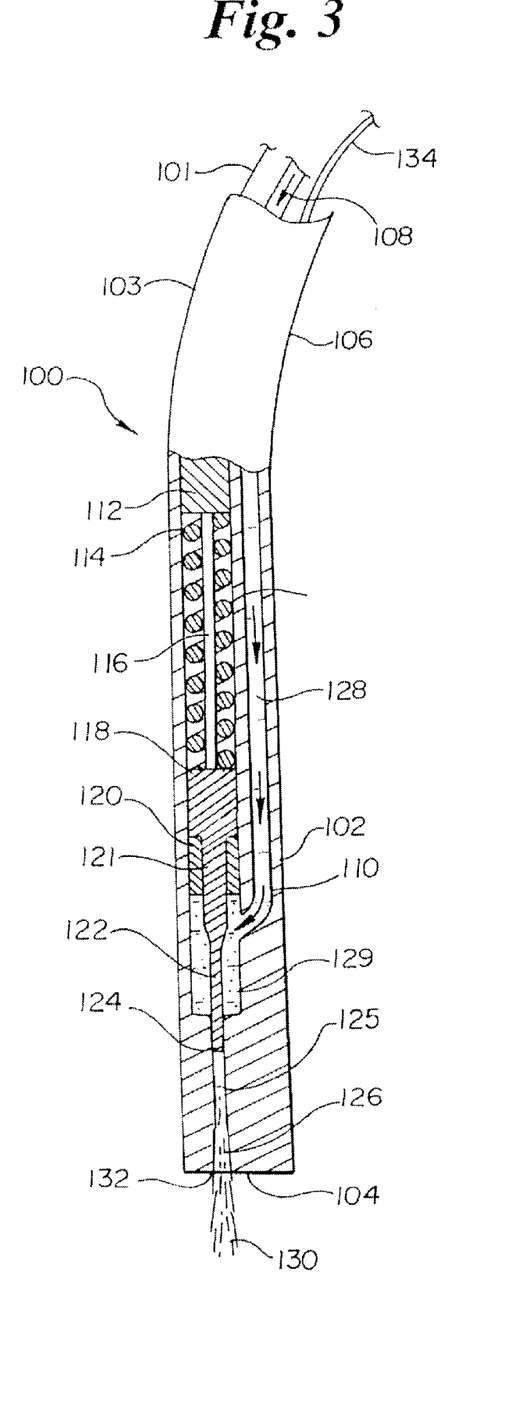
FIG. 3 is a fragmentary, cut-away, longitudinal, cross-sectional view of a fluid jet PMR catheter distal region having a biasing spring and an electrically activated opening mechanism.

Referring now to FIG. 3, a pressure jet PMR catheter 100 is illustrated, having an intermediate region 106, a distal region 102, and a distal tip 104. Pressure jet device 100 includes an outer sleeve or guide catheter portion 103, a pull wire 101, and a pressure supply lumen 108 disposed therein. A valve assembly 110 is disposed in distal region 102, and includes a fixed block 112, coupled to a spring or biasing mechanism 114, also coupled to an electrically actuated control element 116. Biasing spring 114 and control element 116 can both be coupled to a needle valve body 118 which rests in a fixed Block 120 having a lumen 121 therethrough for receiving the needle valve body. Needle valve body 118 can extend distally into a valve stem portion 122 which is illustrated lying within a fluid reservoir portion 129 and also residing within and against a valve seat portion 124, with valve stem 122 occluding a fluid flow lumen 125 disposed within valve assembly 110. A nozzle portion 126 is illustrated, extending distally to a distal-most orifice 132 within distal tip 104. Fluid, under pressure, may be seen to flow through pressure lumen 108, through a pressure fluid intermediate region 128, and into fluid reservoir 129. When valve stem 122 is disposed sufficiently proximal of valve seat 124, fluid flows through lumen 125, and out of orifice 132 as a fluid jet 130.

As can be seen from inspection of FIG. 3, spring 114 acts to bias valve stem 122 in the distal and closed position. Electronic control member or element 116, when activated, can act to retract valve stem 122 from valve seat 124. In one embodiment, control element 116 includes a temperature sensitive, shape memory member. Electrical control element 116 can be supplied by a pair of electrodes 134, with one embodiment having an electrode electrically coupled to opposite ends of the control element. In one embodiment, when electrical potential is applied across the electrical control member, current flows through the control element, thereby raising the temperature, thereby changing the shape of the control element. In one example of the invention, electrical current is passed through a Nitinol wire, which heats and shortens the wire, thereby retracting or shortening control element 116 and retracting valve stem 122. When current is removed, control element 116 can lengthen, thereby shutting valve assembly 110 and precluding fluid flow through the valve. While one embodiment of the invention uses a temperature sensitive element which changes dimensions upon application of electrical potential, other electrically activated devices would be apparent to those skilled in the art. In another embodiment of the invention, not requiring illustration, the biasing spring can bias the valve in the open position, with the control member acting to stop flow through the valve.

In some embodiments, a high pressure fluid within pressure lumen 108 can act to force valve stem 122 proximally out of valve seat 124. In these embodiments, a sufficiently strong biasing spring is used so as to counteract this force. Needle valve 118 can also be dimensioned suitably to provide a small surface area upon which the high pressure can act, thereby reducing the tendency of the pressure fluid to unseat the valve stem until such time as fluid flow is desired by the treating physician.

Figure 4:
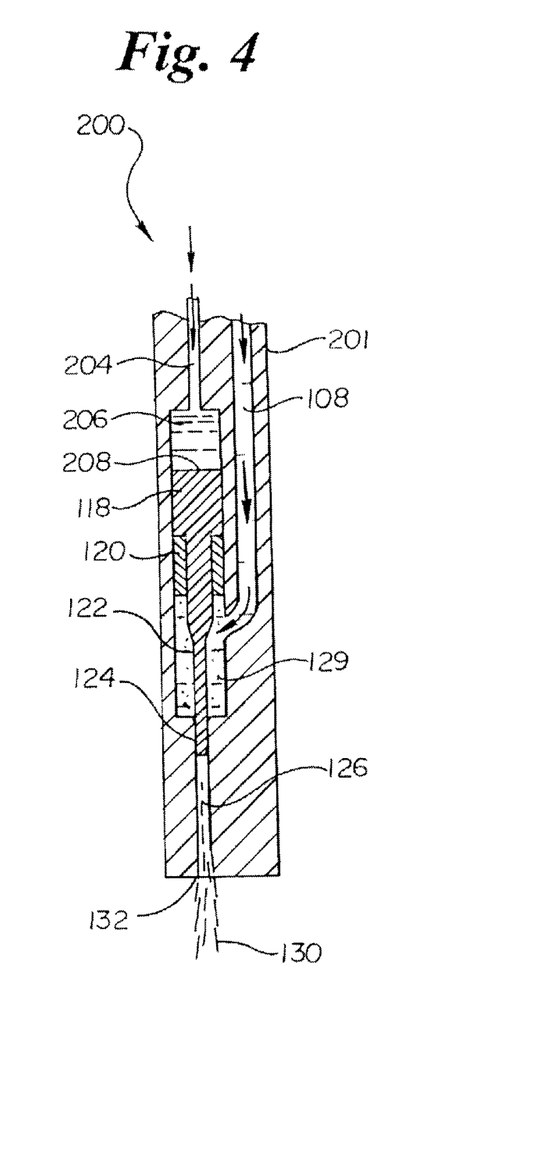
FIG. 4 is a fragmentary, longitudinal, cross-sectional view of a fluid jet PMR catheter distal region having a fluid controlled valve.

Referring now to FIG. 4, another fluid jet PMR device 200 is illustrated. Fluid jet device 200 includes and shares may features of fluid jet device 100 illustrated in FIG. 3. Like numbered elements of FIG. 3 that are repeated in FIG. 4 are so identified and need not be discussed further. Fluid jet PMR device 200 includes generally a catheter shaft 201 having a lower pressure fluid lumen 204 disposed within. Lower pressure lumen 204 is in fluid communication with a fluid accumulator portion 206 within the valve body. Fluid accumulator portion 206 is in communication with, and brings pressure to bear upon, a valve body face region 208.

When sufficiently high control pressure is introduced into lower pressure lumen 204, pressure is brought to bear on valve body 118, acting to force valve stem 122 into valve seat 124. When pressure is sufficiently reduced within pressure lumen 204, valve stem 122 retracts proximally from valve seat 124, thereby allowing high pressure fluid in reservoir 129 and high pressure lumen 108 to extend through nozzle 126, exiting orifice 132 as jet 130. In one embodiment, not requiring additional illustration, a spring, similar to spring 114 of FIG. 3, is disposed within accumulator region 206, thereby acting to bias valve body 118 in a closed, distal position. In another embodiment, fluid must be supplied through lower pressure lumen 204 to maintain valve stem 122 against valve seat 124. In this embodiment, pressure may be substantially reduced so as to allow high pressure flow through nozzle 126.

In yet another embodiment, needle valve body 118 and block 120 are cooperatively sized such that valve stem 122 is at least partially urged from valve seat 124 by high pressure fluid within high pressure lumen 108. In this embodiment, less pressure reduction is required to open the valve to high pressure fluid flow. In one embodiment, negative pressure or vacuum must be applied to lower pressure lumen 204 in order to maintain valve stem 122 in a proximal position clear of valve seat 124. In another example of the invention, lower pressure lumen 204 and high pressure lumen 108 are both provided within separate lumens of a single shaft. In another embodiment, lower pressure lumen 204 and high pressure lumen 108 are defined by separate, metallic, tubes. A preferred metallic tube includes Nitinol. The lower pressure control fluid can be provided from the catheter proximal end and can be controlled using a lower pressure control valve.

Figure 5:
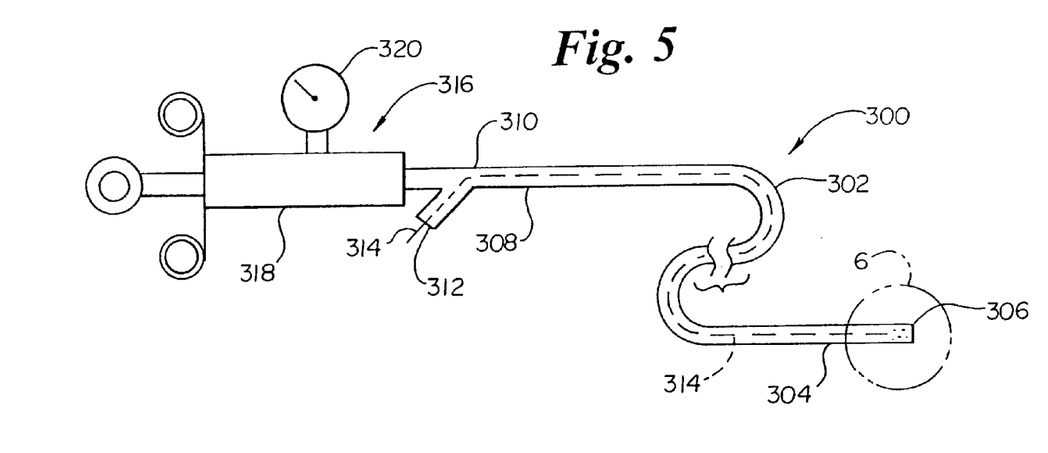
FIG. 5 is a highly diagrammatic, plan view of a fluid jet PMR catheter system having a wire-activated distal valve.

Referring now to FIG. 5, another fluid jet PMR system 300 is illustrated, having a catheter 302 including a proximal region 308, a distal region 304, and a distal end 306. An inflation device such as an Endoflator 316 is illustrated including a pressure gauge 320, and a highly diagrammatic pressure source 318. Catheter 302 includes a proximal manifold 310 having a control port 312, illustrated having an activation wire 314 extending therethrough. Activation wire 314 may be seen to extend the length of catheter 302, terminating within distal region 304. In various embodiments of the invention, activation wire 314 may be either retracted or extended to release fluid pressure from within catheter 302, thereby forcing pressurized fluid out distal end 306. In one embodiment, activation wire 314 is slidably disposed within a lumen within catheter shaft 302.

Figure 6:
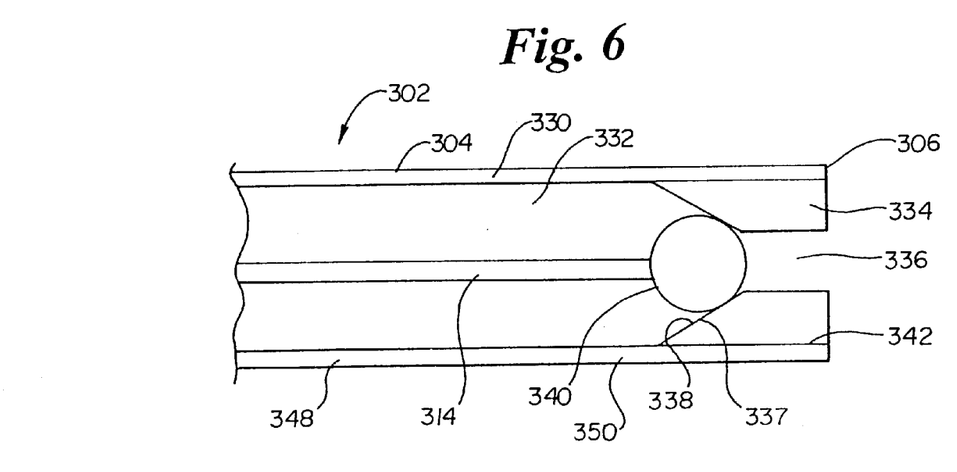
FIG. 6 is a fragmentary, longitudinal, cross-sectional view of a fluid jet PMR catheter distal region having a spherical valve stem seated against a valve seat portion of a nozzle and controlled by an elongate wire valve control member.

Referring now to FIG. 6, distal region 304 of catheter 302 is illustrated. Catheter 302 includes a catheter tube wall 330, having a high pressure lumen 332 defined therein. Catheter 302 terminates distally with a distal valve 334, having a distal-most orifice 336 therein. A valve seat 337 is illustrated having a shoulder region 338 for receiving a valve stem 340. In the embodiment illustrated in FIG. 6, valve seat 337 receives valve stem 340 which prevents fluid from exiting through valve 334. In the illustrated embodiment, valve stem 334 is a substantially spherical element, coupled to an activation wire 314. In one embodiment, activation wire 314 is formed of Nitinol, and valve stem 340 is integrally formed with wire 314 by heating wire 314, thereby causing the wire to melt and form a ball at the distal-most end. In a preferred embodiment, activation wire 314 has sufficient column strength to allow valve stem 340 to be forced against valve seat 337, thereby closing the valve. In another embodiment, not requiring separate illustration, a biasing spring, similar to spring 114 of FIG. 3, is provided within lumen 332 and can be held by a fixed block similar to that illustrated in FIG. 3. In an embodiment having sufficient biasing means, activation wire 314 need only be strong enough to open valve 334, with the closing being accomplished by the biasing spring.

Catheter 302 may also be seen to have a tube wall distal region 348 and a far distal region 350. In one embodiment, far distal region 350 is formed of a more pliant material than distal region 348 disposed proximal of distal region 350. In particular, far distal region 350 can be expanded under pressure so as to substantially increase the distal profile of catheter 302. Catheter wall 330 may also include a bonding region 342 where tube wall 330 is strongly bonded to valve 334.

Figure 7:
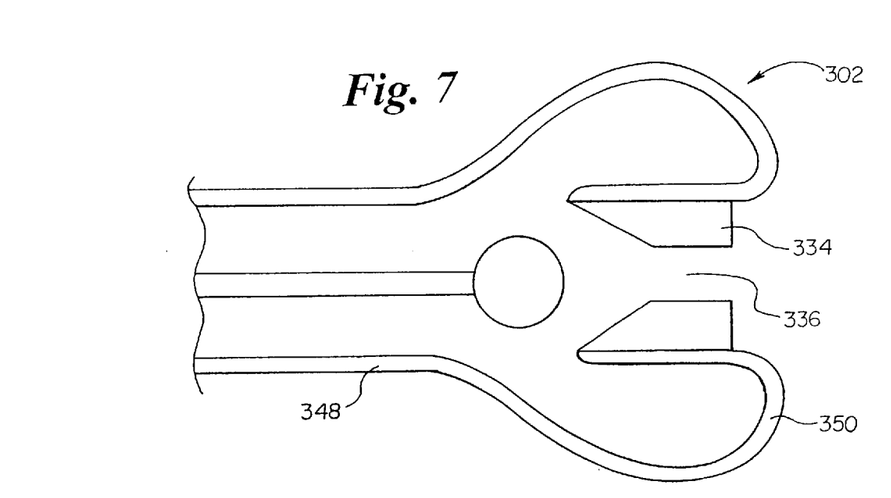
FIG. 7 is a fragmentary, longitudinal, cross-sectional view of the catheter of FIG. 6, shown in an expanded state.

Referring now to FIG. 7, catheter 302 is illustrated in an expanded configuration. In FIG. 7, far distal region 350 has been expanded to have a substantially greater distal cross-sectional profile than the more proximal distal region 348. In one embodiment, far distal region 350 has an unexpanded length of about one-half inch (½). Inspection of FIG. 7 indicates that distal region 348 has not expanded nearly as far as distal region 350, due to the difference of materials between the two regions. In one example, far distal region 350 is formed of an elastomeric substance which recovers the initial dimension upon the reduction of pressure. In another embodiment, far distal region 350 is formed of a material which undergoes plastic deformation under high pressure. As can be seen from inspection of FIG. 7, catheter far distal region 350 can significantly expand under pressure. Catheter distal region 350 can be forced against the heart chamber wall, there providing a better seal about distal nozzle 334 and distal orifice 336. This can significantly improve the seal against the heart wall and around the holes formed in the heart wall. In one embodiment, silicone rubber is included in the walls of far distal region 350. In another embodiment, PEBAX is used in both distal region 348 and far distal region 350, with the far distal region having lower cross-linking PEBAX material than distal region 348. The lower cross-linking can provide a more easily expanded material.

Figure 8:
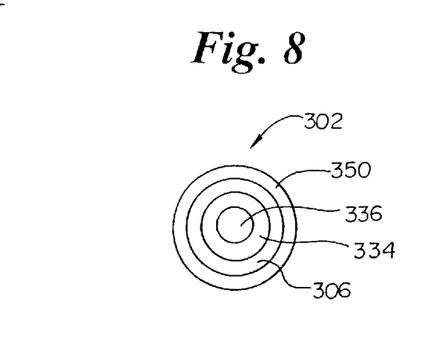
FIG. 8 is an end view of the catheter of FIG. 7, in the expanded state.

Referring now to FIG. 8, catheter 302 is shown from an end view in an expanded state, illustrating central orifice 336 within nozzle 334. Far distal region 350 may be seen to have expanded a distal profile significantly. By providing increased surface area for contact of the catheter distal region against the heart wall, the seal may be improved, and the amount of fluid under pressure that will enter the myocardium can be increased.

Figure 9:
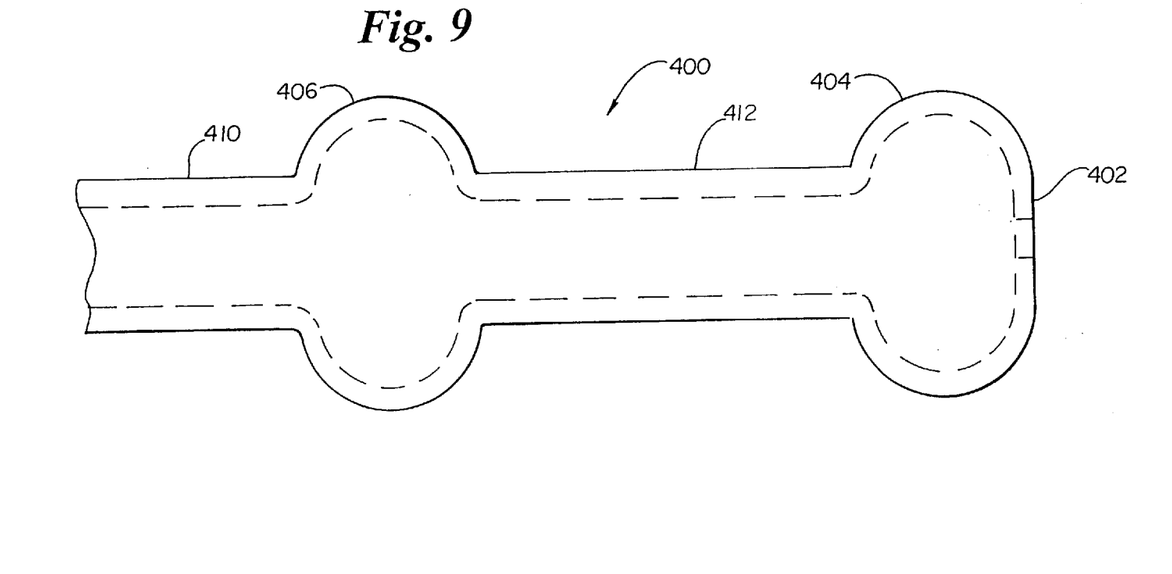
FIG. 9 is a highly diagrammatic, side view of a fluid jet PMR catheter having an expandable intermediate portion for stabilizing the catheter within a guide catheter.

Referring now to FIG. 9, a PMR catheter 400 is illustrated, having a proximal region 410, an intermediate region 406, a distal region 412, a far distal region 404, and a distal end 402. Device 400 may include differing materials of construction as discussed with respect to FIG. 7. Device 400 includes intermediate region 406 formed of a more pliant material, as well as far distal region 404 being formed of a more pliant material. A more rigid material may be found in proximal region 410, as well as distal region 412. The more pliant material may be seen to be employed in regions 406 and 404. Catheter 400 is illustrated in an inflated position. Intermediate, inflatable portion 406 can be disposed about six inches proximal of distal end 402 in one embodiment. In one embodiment, the expandable regions are formed of PEBAX, as are non-expandable regions, with the expandable regions having a significantly lower degree of cross-linking. Expanded intermediate region 406 can serve to expand a catheter until the catheter is expanded against the walls of a containing guide catheter. Expanded region 406 can thus stabilize the distal region of the fluid jet PMR device. With the distal region thus stabilized, fluid being injected from distal end 402 may be counteracted by the secured intermediate region. In particular, the reactionary force from the injecting fluid may be counteracted by the expanded balloon within the guide catheter. In this way, higher pressures, and, in some instance, greater flow rates, may be employed in forming the myocardial holes.

Various fluids may be employed in using the present invention. In one embodiment, saline is used as the high pressure fluid. In another embodiment, saline is combined with therapeutic substances to promote healing and/or angiogenesis within the myocardium. Examples of therapeutic substances include small molecular drugs, proteins, genes and cells which could promote angiogenesis, protect tissues (i.e., cardiac protection), or promote tissue regeneration. Vascular Endothelial Growth Factor (VEGF) and Fibroblast Growth Factors (FGFs) are believed suitable for use with the present invention. Carriers for the therapeutic agents of the present invention can include polymers, angiopoietins, biodegradable and biostable hydrogels, and dissoluble polymers. Adhesives suitable for binding the present invention include fibrin glues and cyanoacrylates which may also be included with the therapeutic substance to improve the desired response. Drug injection catheters referred to in the remainder of the present patent application, and drugs similarly referenced, may include the injection and use of the aforementioned therapeutic substances.

In one embodiment, contrast media is included with the cutting fluid, to provide an indication under fluoroscopy of regions of the heart chamber wall that have been already visited by the fluid jet PMR tip. The contrast media can be injected into holes within the heart wall, which may show up under fluoroscopy.

In an embodiment, a high pressure fluid pressure of at least about 10 atmospheres is used. In some embodiments of the invention, fluid pressure is built up slowly in the distal region of the catheter, and released quickly by use of a distally disposed control valve, as previously discussed. In one example, a distal reservoir region, as indicated in FIGS. 3 and 4, is included to provide a substantial volume of fluid for injecting, even though, in steady state, the high pressure lumen is not sufficiently large to maintain a high flow rate over a long time. The fluid jet PMR fluid may thus be supplied slowly, built up under pressure, and released quickly in jets by a control valve disposed within the catheter. The distal control valve can also have a larger cross-section distal-most orifice than would be possible if this orifice diameter required and maintained the entire length of the catheter. The distal control valve can also provide means for ensuring that the fluid is not injected into the heart chamber until the distal tip is properly positioned.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A system for forming holes in a myocardium of a heart chamber wall, comprising:

a catheter having a proximal region, a distal region and a lumen extending therethrough;

a valve within the lumen of the catheter having a valve seat with an orifice therethrough and a valve stem selectively seated in the valve seat to occlude the orifice; and an elongate central member coupled to the valve stem and extending to the proximal region of the catheter for selectively positioning the valve stem in the valve seat to allow the passage of fluids through the lumen of the catheter in order to form holes in the myocardium of a heart chamber.

2. The system of claim 1, further comprising:

a spring for biasing the valve stem within the valve seat such that the orifice is occluded.

3. A catheter for forming holes in the myocardium of a heart chamber wall, comprising:

an elongate tubular shaft having a proximal region, a distal region, a lumen extending therethrough and a nozzle in fluid communication with the lumen;

a valve disposed along said elongate tubular shaft for controlling fluid flow through said lumen;

a valve actuator for controlling the valve from the proximal region of the elongate tubular member said valve including a valve seat and a valve stem, wherein the valve actuator is coupled to the valve stem.

4. The catheter of claim 3, further comprising a spring for biasing the valve stem in a closed position.

5. The catheter of claim 3, wherein the elongate tubular shaft has a wall that is expandable under pressure and is adapted to engage a guide catheter to stabilize the catheter during use.

6. A system for forming holes in a myocardium of a heart chamber wall, comprising:

a catheter having a proximal region, a distal region and a lumen extending therethrough;

a valve within the lumen for selectively passing liquid through the lumen in order to form holes in the myocardium of a heart chamber; and a valve control for selectively opening and closing the valve including a temperature sensitive member which changes shape in response to changing temperatures and at least one electrode for selectively providing electrical current to the temperature sensitive member in order to heat the temperature sensitive member and open or close the valve.

7. The system of claim 6, further comprising a biasing device for biasing the valve in a closed position.

8. The system of claim 6, wherein the catheter has a wall with at least a first portion and a second portion, said second portion being expandable under pressure to a degree greater than the first portion.

9. A system for forming holes in a myocardium of a heart muscle, comprising:

a catheter having a proximal region, a distal region and a lumen extending therethrough, the catheter having a wall that is expandable under pressure;

a valve disposed in the lumen for allowing passage of fluids in the lumen of the catheter to create holes in the myocardium of a heart muscle;

a guide catheter that is extendable over at least a portion of the catheter; and means for expanding the wall of the catheter such that the wall engages the guide catheter to stabilize the catheter during use.

* * * * *